US009486322B2

(12) United States Patent
Pallia

(10) Patent No.: US 9,486,322 B2
(45) Date of Patent: Nov. 8, 2016

(54) CARPOMETACARPAL PROSTHESIS SYSTEM AND METHOD OF USING SAME

(76) Inventor: Christopher Sterling Pallia, San Diego, CA (US)

(*) Notice: Subject to any disclaimer, the term of this patent is extended or adjusted under 35 U.S.C. 154(b) by 48 days.

(21) Appl. No.: 13/527,265

(22) Filed: Jun. 19, 2012

(65) Prior Publication Data

US 2013/0338784 A1   Dec. 19, 2013

(51) Int. Cl.
*A61F 2/42* (2006.01)
*A61F 2/30* (2006.01)

(52) U.S. Cl.
CPC ........... *A61F 2/4241* (2013.01); *A61F 2/4261* (2013.01); *A61F 2002/30332* (2013.01); *A61F 2002/30495* (2013.01); *A61F 2002/30649* (2013.01); *A61F 2002/4258* (2013.01); *A61F 2002/4276* (2013.01)

(58) Field of Classification Search
CPC . A61F 2/4641; A61F 2002/4264–2002/4297; A61F 2002/4241; A61F 2/4241–2002/4258
USPC .......................... 623/21.11–21.19, 22.43, 23.4
See application file for complete search history.

(56) References Cited

U.S. PATENT DOCUMENTS

| 3,924,276 | A |   | 12/1975 | Eaton |  |
|---|---|---|---|---|---|
| 4,011,603 | A | * | 3/1977 | Steffee | 623/21.16 |
| 4,131,957 | A |   | 1/1979 | Bokros |  |
| 4,276,660 | A | * | 7/1981 | Laure | A61F 2/4241 |
|   |   |   |   |   | 623/21.16 |
| 4,759,768 | A |   | 7/1988 | Hermann et al. |  |
| 4,955,916 | A |   | 9/1990 | Carignan et al. |  |
| 5,405,401 | A |   | 4/1995 | Lippincott, III et al. |  |
| 5,507,822 | A |   | 4/1996 | Bouchon et al. |  |
| 5,645,605 | A |   | 7/1997 | Klawitter |  |
| 8,034,116 | B2 | * | 10/2011 | Vander Meulen et al. | 623/22.43 |
| 2005/0119757 | A1 |   | 6/2005 | Hassler et al. |  |
| 2005/0251265 | A1 |   | 11/2005 | Calandruccio et al. |  |
| 2006/0241777 | A1 | * | 10/2006 | Partin et al. | 623/21.11 |
| 2007/0021839 | A1 |   | 1/2007 | Lowe |  |
| 2008/0221698 | A1 | * | 9/2008 | Berger | 623/21.19 |
| 2011/0106268 | A1 | * | 5/2011 | Deffenbaugh et al. | 623/20.32 |

(Continued)

FOREIGN PATENT DOCUMENTS

| JP | 07-000435 | 1/1985 |
|---|---|---|
| JP | 64-046452 | 2/1989 |
| JP | 06-075564 | 3/2006 |

OTHER PUBLICATIONS

Dror Lakstein, et al., 2011, Fracture of Cementless Femoral Stems at the Midstem Junction in Modular Revision Hip Arthroplasty Systems, 20 Pickering Street, Needham, MA, U.S.A.

(Continued)

*Primary Examiner* — Christopher D Prone
(74) *Attorney, Agent, or Firm* — Jerry R. Potts; James R. McDaniel

(57) ABSTRACT

A carpometacarpal prosthesis system generally includes a trapezial implant for replacing an excized trapezium within a human hand and a component stem implant for replacing a partially excized first metacarpal. The component stem implant is adapted to be press fit within the medullary cavity of the partially excized first metacarpal bone of the human hand; the component stem when so implanted is adapted to effect universal movement of the first metacarpal bone relative to the trapezial implant thereby providing a restructured thumb metacarpal joint that restores substantially normal thumb function in terms of strength and flexibility.

11 Claims, 7 Drawing Sheets

(56) References Cited

U.S. PATENT DOCUMENTS

| | | | |
|---|---|---|---|
| 2011/0112652 A1 | 5/2011 | Hansson et al. | |
| 2011/0172782 A1* | 7/2011 | Klawitter et al. | 623/21.15 |
| 2013/0197655 A1* | 8/2013 | Scheker | 623/21.16 |

OTHER PUBLICATIONS

[on line] The Journal of Bone and Joint Surgery, vol. 93-A, No. 1, Jan. 5, 2011 available at http://www/emg/tau.ac.il/~neliaz/Papers_Files/Dror%20JBJS.pdf.

S.W. Wachtl, et al., 1998, Cemented and Non Cemented Replacements of the Trapeziometacarpal Joint, Chirugie St. Leonhard, St. Gallen, Switzerland.

[on line] The Journal of Bone and Joint Surgery, vol. 80-B, No. 1, Jan. 1988, available at http://web.jbjs.org.uk/content/89-B/1/121.full.pdf.

Small Bone Innovations, Inc., 2012, Avanta CMC [online] Small Bone Innovations, Inc. available at http://totalsmallbone.com/us/products/thumb/avanta_cmc.php4.

O. Bostman, "Clinical biocompatibility of biodegradable orthopaedic implants for internal fixation: a review", Biomaterials, 2000, pp. 2615-2621, vol. 21, Elsevier Science.

G.O. Hofmann, "Biodegradable implants in traumatology:a review on the state-of-the-art", Arch Orthop Trauma Surg, 1995, pp. 123-132, vol. 114, Springer-Vertag, US.

* cited by examiner

CARPOMETACARPAL PROSTHESIS SYSTEM AND METHOD OF USING SAME

FIELD OF THE INVENTION

This invention relates generally to prosthesis systems and more particularly to a thumb prosthesis system for restoring substantially normal thumb function following the effects of injury to or disease in the carpometacarpal joint of the thumb.

BACKGROUND OF THE INVENTION

There have been many different types and kinds of thumb prosthesis systems. Such systems typically seek to provide a patient with a restructured thumb metacarpal joint which functions to provide a patient with satisfactory strength and flexibility. For example, reference may be made to the following U.S. Pat. No. 3,924,276 by Eaton; U.S. Pat. No. 4,011,603 by Steffe; U.S. Pat. No. 4,131,957 by Bokros; U.S. Pat. No. 4,276,660 by Laure; U.S. Pat. No. 4,759,768 by Hermann, et al.; U.S. Pat. No. 4,955,916 by Carignan, et al.; U.S. Pat. No. 5,405,401 by Lippincott, III, et al.; U.S. Pat. No. 5,507,822 by Bouchon, et al.; U.S. Pat. No. 5,645,605 by Klawitter; U.S. Pat. No. 5,913,858 by Calandruccio et al.; U.S. Pat. No. 7,182,787 by Hassler et al.; U.S. Pat. No. 8,021,431 by Townley and U.S. Pat. No. 8,034,116 by Vander Meulen et al. While such prosthesis systems may have been generally satisfactory, there is nevertheless a need for a new and improved thumb prosthesis system for helping to restore substantially normal thumb function following the effects of injury to or disease in the carpometacarpal joint of the thumb.

SUMMARY OF THE INVENTION

A carpometacarpal prosthesis system of the present invention generally includes a trapezial implant for replacing an excised trapezium and a component stem which is adapted to be implanted within a partially excised first metacarpal bone of a human hand; the component stem when so implanted is adapted for universal movement relative to the trapezial implant.

A feature of the present invention is the provision of a component stem which is generally tapered throughout its entire longitudinal length and which is configured to be received in a friction tight fit within the medullary cavity of the first metacarpal bone in a human hand. In this regard, the stem generally has a greater diameter at its proximal end than at its distal end. The proximal end of the component stem terminates in an integrally attached flanged collar.

Another feature of the present invention is the provision of a component stem which is composed of a material with a surface texture to facilitate bone ingrowth.

Yet another feature of the present invention is the provision of a component stem which has a porous surface texture.

According to another aspect of the present invention there is provided a carpometacarpal prosthesis system the flanged collar is integrally connected opposite the component stem to an elongated neck having a sufficient longitudinal length to help restore an excised length of bone previously disposed at about a proximal end portion of the first metacarpal bone; the elongated neck being integrally connected opposite the flanged collar to a spherically shaped head; wherein the head is adapted to be received within said trapezial implant for facilitating universal movement between the component stem and the trapezial implant.

Another feature of the present invention is the provision that the component stem has a sufficient longitudinal length to be received in a friction-tight fit within an elongate centrally disposed tapered cavity formed in the first metacarpal bone.

Yet another feature of the present invention is that the sufficient longitudinal length of the component stem is no greater than a midpoint length of the first metacarpal bone.

A feature of the present invention is the provision that the flanged collar has a sufficient diameter to facilitate its permanent attachment relative to an exposed cut base bone area in the first metacarpal.

Another feature of the present invention is the provision that the contour of the stem facilitates a good press fitting of the component stem into the intramedullary cavity formed in the first metacarpal bone.

Yet another feature of the present invention is the provision that the flanged collar is configured to substantially prevent subsidence or motion of the stem in the metacarpal in cases where it is cemented or when the contour is just slightly small for an excellent press fit.

Still yet another feature of the present invention is that the component stem has a sufficient standardized surface roughness for facilitating bone ingrowth.

A feature of the present invention is the provision that the standardized surface roughness of the component stem is a grit-blasted surface.

Another feature of the present invention is the provision that the flanged collar is disposed slightly proud of the cortical bone so that cyclic loading of an implant bone interface between the partially excised first metacarpal and the collar will stimulate bony ingrowth there between.

According to another aspect of the present invention there is provided a carpometacarpal prosthesis system, comprising: a trapezial implant configured substantially to the same size and shape of an excised trapezium to facilitate replacement of the excised trapezium with said trapezial implant; and where the trapezial implant has a substantially centrally disposed socket for receiving therein a spherical head of a stem component adapted to be implanted within a first metacarpal of a human hand to facilitate universal movement between the stem component and the trapezial implant.

A feature of the present invention is the provision that the stem component has a unitary construction and an overall longitudinal length of about one half the length of said first metacarpal.

Another feature of the present invention is the provision that the trapezial implant is provided with a plurality of articulating surfaces.

Yet another feature of the present invention is the provision that each articulating surface of the trapezial implant is a smooth surface to facilitate articulating action.

Still yet another feature of the present invention is the provision that the stem component has a unitary construction and an overall longitudinal length that substantially corresponds to said first metacarpal.

A feature of the present invention is the provision that the stem component is composed of a body tolerant material selected from a group of body tolerant materials consisting of cobalt/chrome, titanium, tantalum or a nickel alloy.

Another feature of the present invention is the provision that the trapezial implant is composed of another body tolerant material selected from another group of body tolerant materials consisting of polyethylene, a cobalt/chrome alloy or a ceramic.

According to another aspect of the present invention there is provided a carpometacarpal prosthesis system, comprising: an elongate body member having a unitary construction, the elongate body member is adapted for an intramedullary cavity fit within a first metacarpal of a human hand; wherein said elongate body member generally comprises: an elongate tapered stem; a flange like collar integrally connected to a proximal end part of said stem; an elongated neck integrally connected to the collar spaced from the proximal end part of said stem to form an elongate metacarpal insert; and a spherical shaped head integrally connected to a proximal end of the elongated neck; wherein the head is dimensioned to be received lockingly within a trapezial implant having substantially the same size of an excised trapezium removed from the human hand.

A feature of the present invention is the provision that the head and the neck are selectively sized relative to the excised portion of said first metacarpal and said excised trapezium to facilitate restoring a normal length thumb with relation to a thumb being partially excised for the prosthesis system.

Another feature of the present invention is the provision that the trapezial implant is provided with a socket with a locking mechanism to lockingly receive therein said head.

Yet another feature of the present invention is the provision that the trapezial implant is adapted with a socket which is dimensioned to lockingly receive therein the head.

Still yet another feature of the present invention is the provision that the trapezial implant is composed of a body tolerant material with some surface roughness to facilitate bonding of scar tissue to said trapezial implant.

A feature of the present invention is the provision that a base portion of the trapezial implant is configured to stimulate natural anatomy to articulate within a convex distolateral surface area of an adjacent scaphoid to facilitate substantially pain free movement between said trapezial implant and the adjacent scaphoid.

Another feature of the present invention is the provision that the trapezial implant cooperates with a proximal surface area of an adjacent trapezoid to form a concave surface for articulation with a convex distal articular surface area of said scaphoid to further facilitate pain free movement between said trapezial implant and the adjacent scaphoid and trapezoid.

According to another aspect of the present invention there is provided a method of diminishing pain, comprising the steps of: excising a trapezium forming part of a degenerated carpometacarpal joint; replacing the excised trapezium with a trapezial implant, the trapezial implant having substantially the same size and shape as the excised trapezium; and excising a proximal end portion of a first metacarpal forming part of the degenerated carpometacarpal joint; and coupling an elongate stem component between said trapezial implant and a remaining first metacarpal segment resulting from the last mentioned step of excising to facilitate substantially pain free universal moment between the remaining first metacarpal segment and said trapezial implant.

A feature of the present invention is the provision that the step of excising a proximal end portion of a first metacarpal includes forming a substantially flat base surface on the remaining first metacarpal segment.

Another feature of the present invention is the provision that the step of coupling includes: drilling a centrally disposed tapered cavity commencing at the base surface of the remaining first metacarpal and extending inwardly along a longitudinal axis of the remaining first metacarpal a sufficient distance to facilitate receiving in friction-tight fit within said cavity at least a portion of said elongate stem component but not a sufficient distance so that said at least a portion of said elongate stem component extends beyond a midpoint longitudinal plane of the remaining metacarpal segment.

Yet another feature of the present invention is the provision that the elongate stem component has a unitary construction that includes: an elongate tapered body member adapted for an intramedullary cavity fit within the remaining metacarpal segment; a flange like collar integrally connected to a proximal end part of said body member; an elongated neck integrally connected to the collar spaced from the proximal end part of the body member; and a spherical shaped head integrally connected to a proximal end of the elongated neck.

Still yet another feature of the present invention is the provision that the step of coupling further includes: inserting by press fit said elongate tapered body member into the tapered cavity disposed in the remaining metacarpal segment to help facilitate substantially pain free universal movement between the remaining metacarpal segment and said trapezial component; and inserting lockingly by press fit the head into a socket disposed in the trapezial implant to further help facilitate substantially pain free universal movement between the remaining metacarpal segment and the trapezial implant.

A feature of the present invention is the provision that the step of excising a trapezium forming part of the degenerated carpometacarpal joint and the step of excising a proximal end portion of a metacarpal forming part of the degenerated carpometacarpal joint in combination result in the excising of the degenerated carpometacarpal joint.

Another feature of the present invention is the provision that the trapezial implant is composed of a body tolerant material with some surface roughness to facilitate bonding of scar tissue to the trapezial implant.

Still yet another feature of the present invention is the provision that the head and the elongated neck are selectively sized relative to the excised portion of said first metacarpal and said excised trapezium to facilitate restoring a normal length thumb with relation to a thumb being partially excised for the prosthesis system.

Another feature of the present invention is the provision that the step of inserting by press fit said elongate tapered body member into the tapered cavity disposed in the remaining metacarpal segment includes positioning the flanged collar proud of the substantially flat base surface on said remaining first metacarpal segment so that cyclic loading of a resulting implant bone interface between the remaining first metacarpal segment and said collar will stimulate bony ingrowth therebetween.

Still yet another feature of the present invention is the provision that the elongate tapered body member is a grit-blasted tapered body member.

According to another aspect of the present invention there is provided a carpometacarpal prosthesis system, comprising: an elongate stem component having a unitary construction; the elongate stem component including: an elongate tapered body member adapted for an intramedullary fit within a first metacarpal segment; a flange like collar integrally connected to a proximal end part of said body member; an elongated neck integrally connected to said collar spaced from said proximal end part of said body member; and a spherical shaped head integrally connected to a proximal end of the elongated neck.

A feature of the present invention is the provision that the spherical shaped head is adapted to be inserted lockingly by press fit into a socket of a polyethylene trapezial implant to help facilitate substantially pain free universal movement between the first metacarpal segment and said trapezial implant.

Still yet another feature of the present invention is the provision that the stem component has a selected overall longitudinal length of about one half the length of the pre-cut metacarpal.

Yet another feature of the present invention is the provision that the elongate tapered body member is provided with a rough textured surface.

Another feature of the present invention is the provision that the said rough textured surface is a grit-blasted surface.

Another feature of the present invention is the provision that the said rough textured surface is a standard surface roughness preparation utilized on arthroplasty implants.

A feature of the present invention is the provision that the spherical shaped head is composed of either a ceramic material or a metallic material such as a titanium material or a cobalt/chrome material.

According to another aspect of the present invention there is provided a prosthesis for use in a carpometacarpal prosthesis system, comprising: a trapezial implant configured substantially to the same size and shape of an excised trapezium to facilitate replacement of the excised trapezium with said trapezial implant; and the trapezial implant having a centrally disposed locking mechanism socket to facilitate the coupling of the trapezial implant to a first metacarpal implant so that the first metacarpal implant has a range of universal movement about the trapezial implant.

A feature of the present invention is the provision that the trapezial implant is composed of a body tolerant material with some surface roughness to facilitate bonding of scar tissue to said trapezial implant.

Another feature of the present invention is the provision that the surface roughness is a grit-blasted surface.

Yet another feature of the present invention is the provision that a base portion of said trapezial implant is configured to simulate natural anatomy to articulate within a convex distolateral surface area of an adjacent scaphoid to facilitate substantially pain free movement between the trapezial implant and the adjacent scaphoid.

Still yet another feature of the present invention is the provision that the trapezial implant cooperates with a proximal surface area of an adjacent trapezoid to form a concave surface for articulation with a convex distal articular surface area of the scaphoid to further facilitate pain free movement between the trapezial implant and the adjacent scaphoid and trapezoid.

And yet still another feature of the present invention is the provision that the trapezial implant is composed on a body tolerant material selected from a group of body tolerant materials consisting of ceramic, titanium, polyethylene or a cobalt/chrome alloy.

BRIEF DESCRIPTION OF DRAWINGS

The above mentioned features and steps of the invention and the manner of attaining them will become apparent, and the invention itself will be best understood by reference to the following description of the embodiments of the invention in conjunction with the accompanying drawings wherein.

DETAILED DESCRIPTION OF PREFERRED EMBODIMENTS

Figure 1:
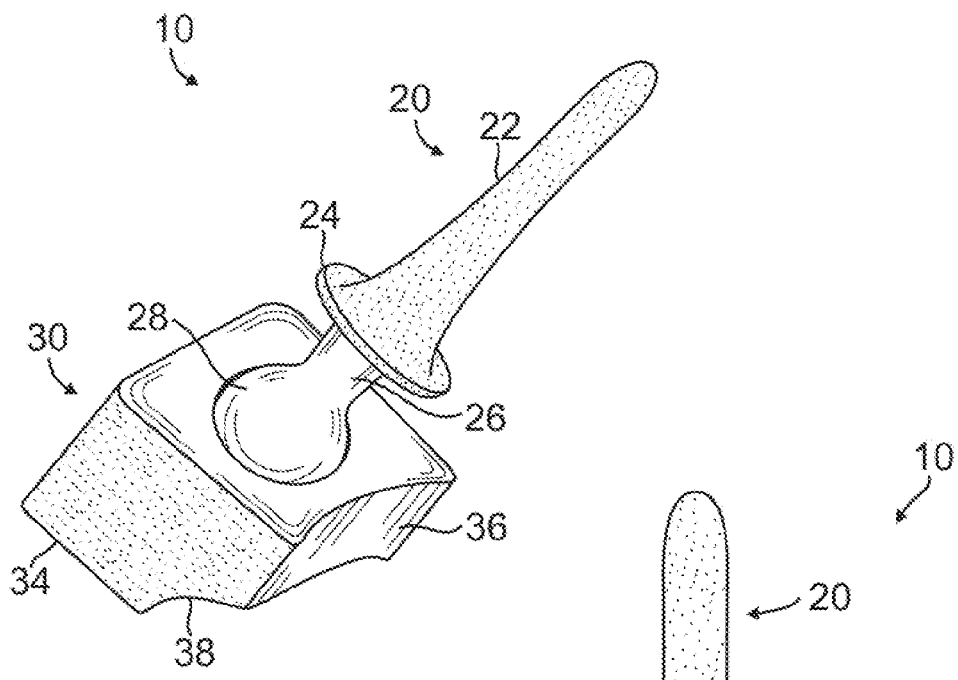
FIG. 1 is a perspective view of a customized $1^{st}$ carpometacarpal arthroplasty system constructed according to the present invention.
Figure 2:
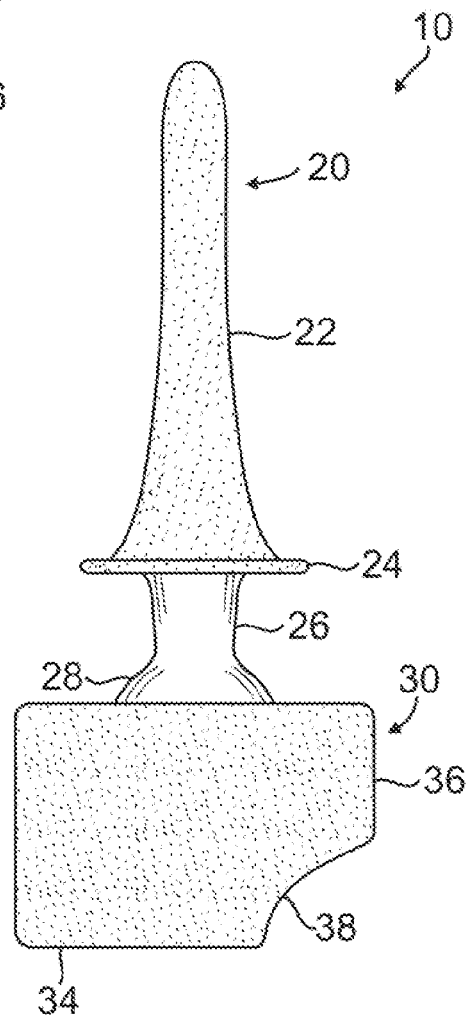
FIG. 2 is a side elevational view of the customized carpometacarpal system of FIG. 1.

Referring now to the drawings and more particularly to FIGS. 1-2 there is illustrated a carpometacarpal prosthesis system 10, which is constructed in accordance with the present invention. The carpometacarpal prosthesis system 10 when used in accordance with a novel method of using the system 10 to restore in a much more efficient and less time consuming manner substantially normal thumb function following the effects of injury to or disease in the carpometacarpal joint of the thumb. In accordance with the use of the prosthesis system 10, the system 10 obtains several advantages. For example, when implanted, the carpometacarpal prosthesis system 10 is solid and stable. Also, the configuration of the prosthesis system 10 simulates the body's natural anatomy, so that the thumb can articulate without causing pain. In addition, the carpometacarpal prosthesis system 10 allows some bonding of scar tissue to enhance effectiveness and service life of the prosthesis. Further, suitable sizing of the carpometacarpal prosthesis system 10 can give the thumb muscle increased power and strength following surgery. Most importantly, the utilization of the new and improved carpometacarpal prosthesis system 10 can greatly reduce the surgical time required to implant the device in a patient.

Figure 8:
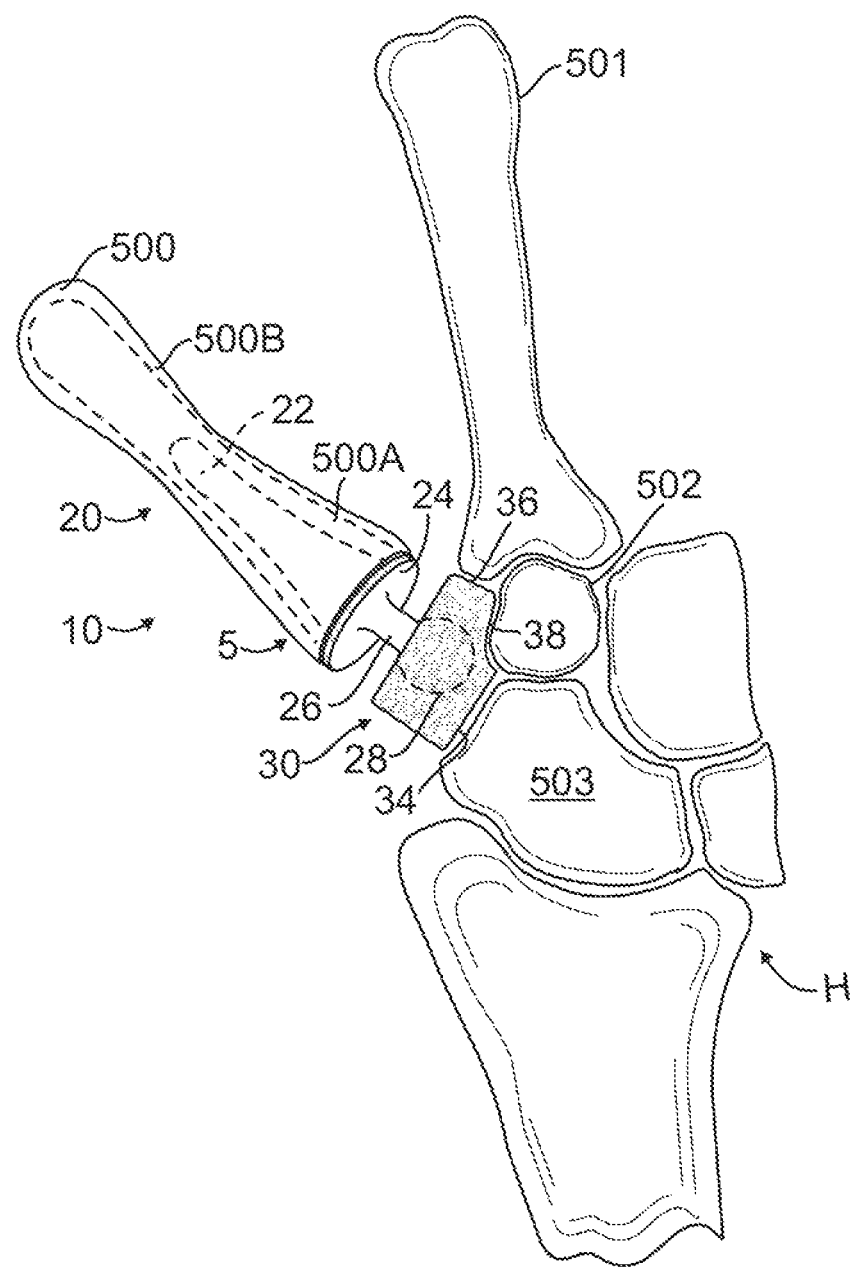
FIG. 8 is a diagrammatic view of the customized $1^{st}$ carpometacarpal arthroplasty system as implanted in the hand of a patient.

Considering now the carpometacarpal prosthesis system 10 in greater detail with reference to FIGS. 1-3 and 8, the carpometacarpal prosthesis system 10 generally comprises a component stem implant 20 and a trapezial implant 30. As best seen in FIG. 8, the component stem implant 20 is adapted to be implanted in the intramedullary canal 500B of a partially excised first metacarpal bone 500 of the hand H of a patient, while the trapezial implant 30 is configured for replacement of a completely excised trapezium bone in the hand of the patient. In this regard, the component stem 20, when implanted in combination with the trapezial implant 30, is adapted for universal movement relative to the trapezial implant 30 thereby simulating the body's natural anatomy, so that a patient's previously injured or diseased thumb can articulate without causing any substantial pain. The proximal end of the first metacarpal bone 500 is excised to provide the proximal end of the first metacarpal bone 500 with a substantially flat base. The amount of bone cut off from the first metacarpal bone 500 is determined by the operating room surgeon.

Figure 3:
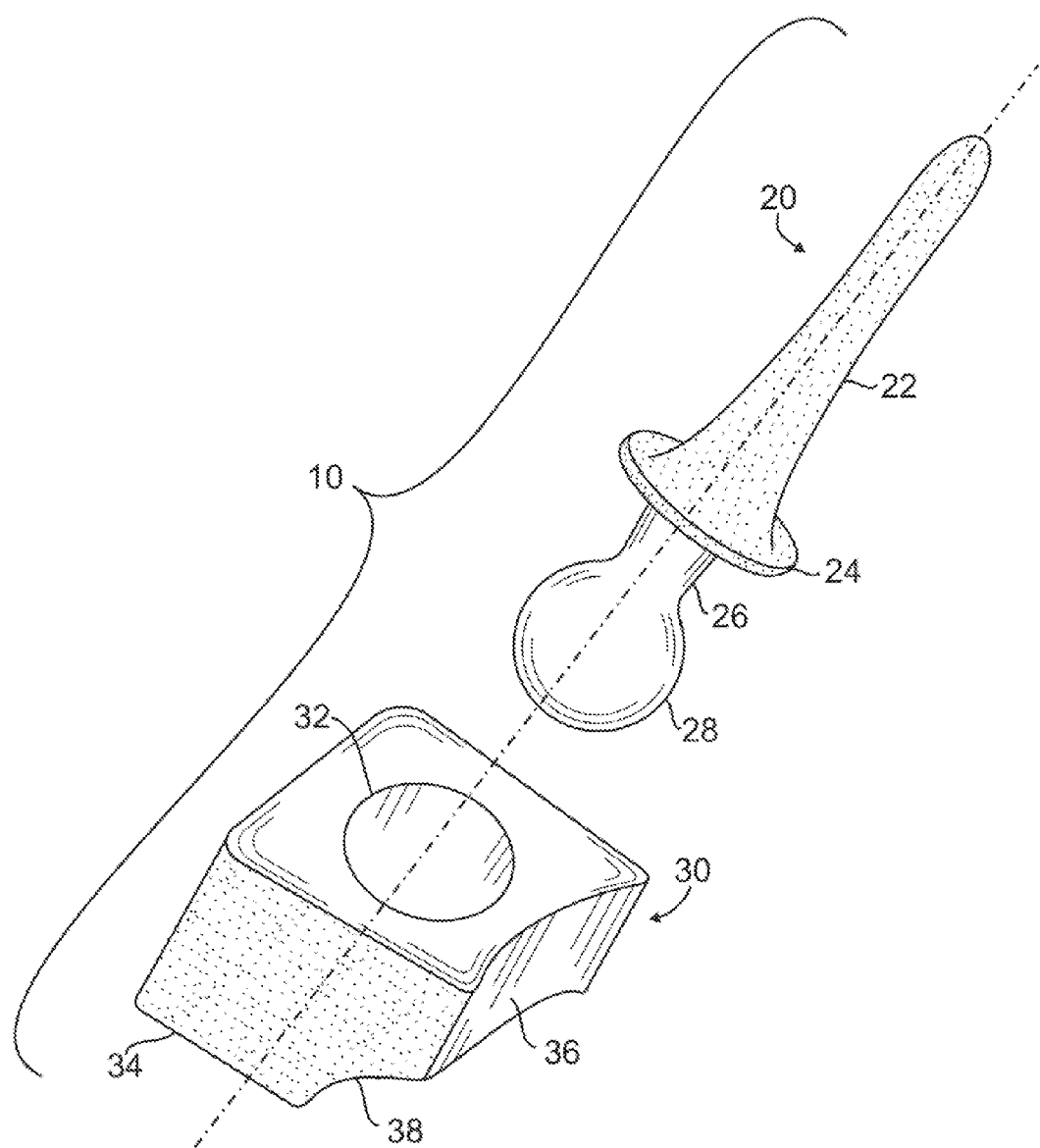
FIG. 3 is an exploded view of the customized carpometacarpal system of FIG. 1.
Figure 4:
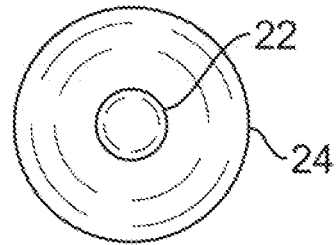
FIG. 4 is a top plane view of a stem component implant forming part of the carpometacarpal system of FIG. 1.
Figure 5:
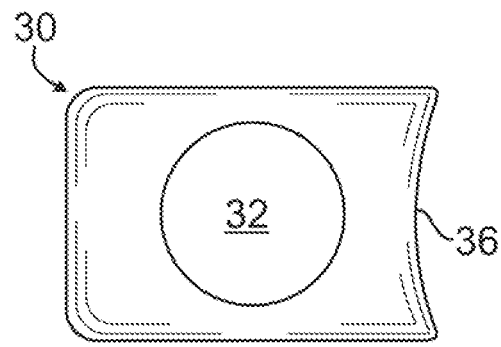
FIG. 5 is a top plane view of a trapezial implant forming part of the carpometacarpal system of FIG. 1.
Figure 6:
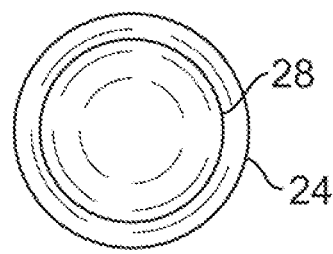
FIG. 6 is a bottom plane view of the stem component implant of FIG. 4.
Figure 7:
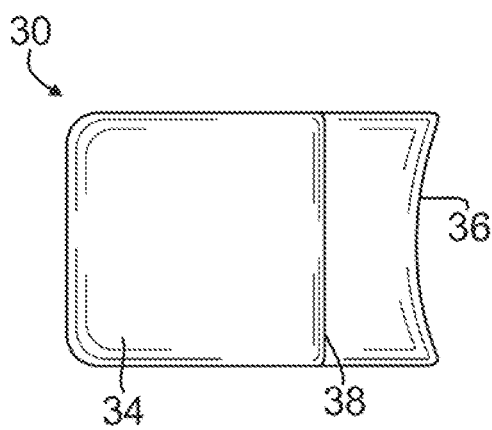
FIG. 7 is a bottom plane of the trapezial implant of FIG. 5.

Considering now the stem component 20 in greater detail with reference to FIGS. 1-3, the stem component implant 20 is composed of a body inert material such as a titanium material or a cobalt/chrome material that will not be rejected by the human body. As best seen in FIG. 1, the stem component 20 has a unitary construction that generally includes a set of integrally connected component parts that are aligned along a common longitudinal axis 40. The set of integrally connected component parts include an elongated tapered stem 22, a flanged collar 24, an elongated neck 26 and a spherical head 28. As noted earlier, the stem component 20 is sized a friction tight fit in the intramedullary canal 500B of a partially excised first metacarpal bone 500. In this regard, via the flanged collar 24, the stem 22 is press fit within the intramedullary canal 500B a sufficient distance to help restore that portion of the first metacarpal bone 500 that was excised. In general however, the length of the stem 22 should not be longer than the midpoint of the metacarpal (central diaphysis). As best seen in FIGS. 1-3, the stem 22 is provided with a standardized surface roughness which is proven for excellent bone ingrowth from hip replacement experience. This surface roughness can be provided by any standard surface roughness preparation technique used in arthroplasty implants or by, for example, grit-blasting the surface. If needed in the opinion of the implanting surgeon, the stem 22 may also be cemented within the intramedullary canal 500B. In this regard, for cementing purposes a cement restrictor may be utilized for an osteoporotic bone or a bone whose canal is too large for the above-described press fitting procedure.

The stem 22 is tapered and is closely configured to the exact shape of the intramedullary canal 500B of the hand H of the patient. In this regard the stem 22 is narrower at its distal end than at its proximal end. The proximal end of the stem 22 in this regard, is integrally connected to the flanged collar 24. This particular stem/collar configuration is selected so that when the stem 22 is press fit the correct distance into the intramedullary canal 500B the flanged collar 24 will rest against the cut bone surface of the first metacarpal bone 500. In some cases however, the flanged collar may be proud of the flat base surface of the metacarpal bone 500. In either case the use of the thumb following surgery should lead to cyclic loading of the implant bone interface, thereby stimulating bony ingrowth.

As best seen in FIGS. 1-3 the flanged collar has a generally circular shape with a substantial underside lip area which may be grasped by the operating room surgeon for press fitting the stem 22 into the intramedullary canal 500B. This underside lip area is also integrally connected to the elongated neck 26 of the stem component 20. The opposite end of the elongated neck 26 is integrally connected to the spherical head 28. The neck/head configuration is further selected based upon the amount of bone excised from the proximal end of the first metacarpal bone 500 and the size of the trapezial implant utilized to replace the injured or disease trapezium. In this regard, the neck/head configuration and more particularly the neck length is selected based upon the amount of bone cut off the base of the metacarpal and the size of the trapezial implant 30 to effectively restore the normal length of the thumb before excising. Adding a small amount of extra length to the restored thumb by increasing the length of the elongated neck 26 will have the advantageous effect of give attached muscles of the thumb increased power and strength which is considered a important feature of the present invention.

Considering the trapezial implant 30 in still greater detail, the trapezial implant 30 is composed of an inert material suitable for use in the human anatomy. In this regard, the trapezial implant material is selected from a group of suitable materials such as a polyethylene material, a ceramic material, titanium and a cobalt-chrome material. It should be understood that other materials could be utilized so long as the material is suitable for use in the human anatomy; accordingly, there is no intention of limiting the selected materials to only those that have been listed herein.

To facilitate the body's natural anatomy, the prosthesis system 10, and more particularly the trapezial implant 30 is configured substantially to the same size and shape of the excised trapezium. As noted above, the trapezial implant 30 is a composed of a polyethylene material and is configured to articulate with the base of the second metacarpal bone 501, the trapezoid bone 502 and the scaphoid bone 503 of the hand H of the patient. In this regard, the trapezial implant 30 will simulate natural anatomy to articulate with these bones of the hand H without causing pain. The outer surface of the trapezial implant 30 is also provided with a rough surface texture to facilitate the bonding of scar tissue to the implant 30.

To enable the trapezial implant 30 to articulate with the bones of the hand H, the trapezial implant is provided with smooth rounded corners and surfaces as well as various cutout area that enable the trapezial implant 30 to smoothly and easily articulate with the surrounding hand bones. More particularly, the trapezial implant 30 is provided with a $2^{nd}$ metacarpal articulating surface cut out area indicated generally at 36 for engaging a lower left quadrant area of the $2^{nd}$ metacarpal bone 501 as best seen in FIGS. 1 and 8.

In a similar manner to enable the trapezial implant 30 to articulate with the trapezoid bone 502, the trapezial implant 30 is provided with a trapezoid bone articulating surface cutout area 38 which is also provided with substantially smooth rounded corners.

In order to enable the trapezial implant 30 to articulate with the scaphoid bone 503, the trapezial implant 30 is provided with a substantially smooth bottom surface area indicated generally at 34.

Finally, in order to allow universal movement between the stem component implant 20 relative to the trapezial implant 30, the trapezial implant 30 is further provided with a centrally disposed ball and socket arrangement. This arrangement enables the head 28 of the stem component 20 to enjoy universal movement within a trapezial implant socket indicated generally at 32. The socket 32 is adapted to receive therein the spherical head 28 of the stem component 20. In this regard, the head 28 is locked into the socket 32 much like a ball is locked into a bipolar hemiarthroplasty. More particularly, the head 28 is popped into place within the socket 32 using a convenient counter in the operating room environment. Once the ball or head 28 is anchored within the socket 32, the head and socket arrangement will provide a pure basal joint range of motion based on measured clearances, the neck diameter and the polyethylene opening designs. Such procedures for interconnecting a ball and socket implant arrangement are well known to skilled surgeons and will not be described hereinafter with any further detail.

Figure 9:
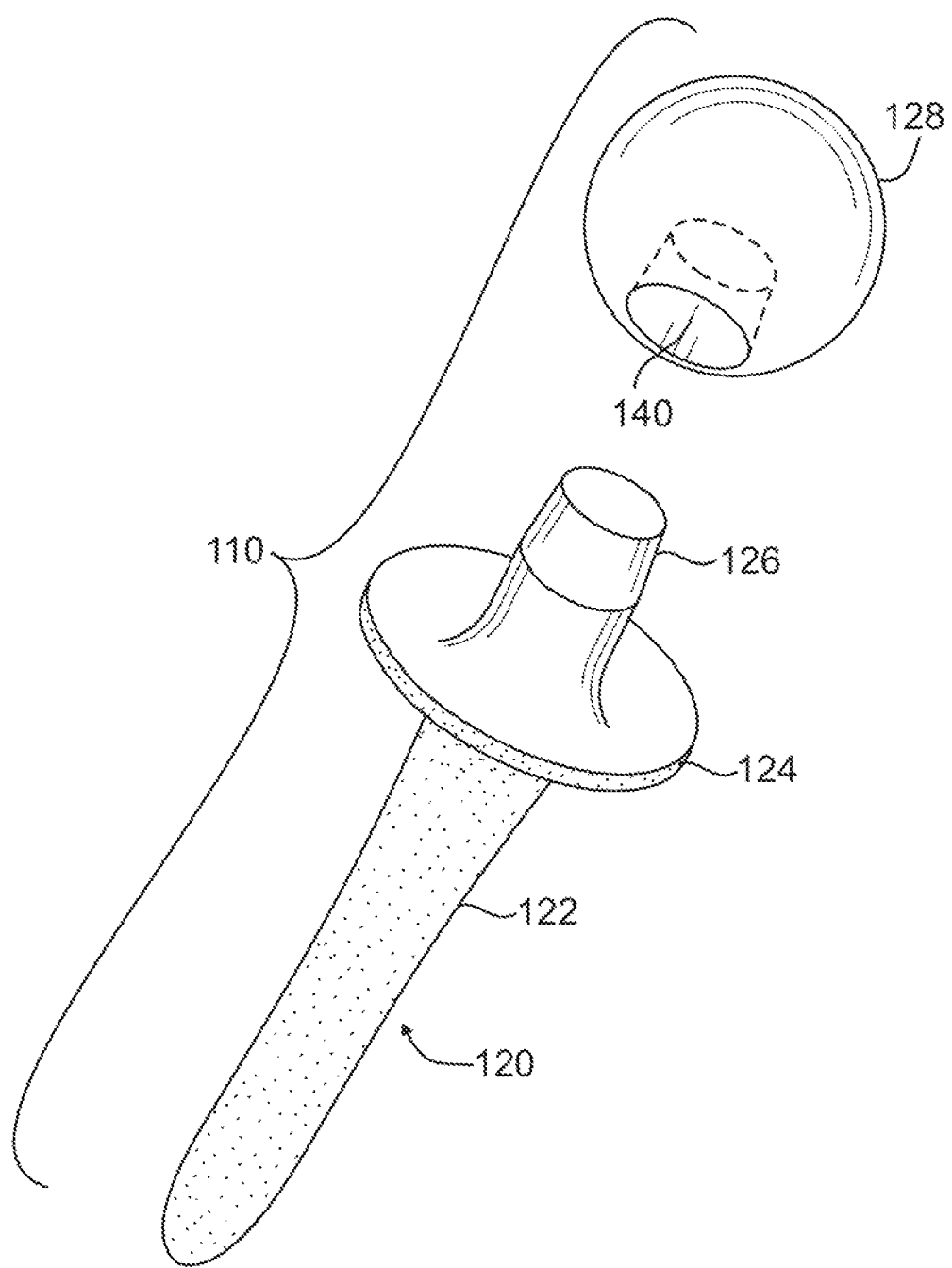
FIG. 9 is a perspective view of another customized $1^{st}$ carpometacarpal arthroplasty system constructed according to the present invention.

Referring now to the drawings and more particularly to FIG. 9 there is illustrated a carpometacarpal prosthesis system 110, which is constructed in accordance with the present invention. The prosthesis system 110 is substantially similar to the prosthesis system 10 except rather than having a stem component with a unitary construction, the prosthesis system 110 is provided with a trapezial implant 130 and a stem component implant 120 with a non unitary construction. In this regard, the stem component implant 120 generally includes a porous type stem 122, which is integrally connected to a flanged collar 124. The opposite side of the flanged collar 124 is integrally connected to a centrally disposed neck having at its opposite end a Morse taper neck 126 at its neck-head junction. As will be explained hereinafter this Morse taper neck 126 at the neck-head junction is configured to receive thereon a removable ceramic head 128.

In this $2^{nd}$ embodiment of the present invention, the stem component implant 120 is composed of either a cobalt/chrome material or titanium material except for its head 128 which is composed of a ceramic material as mentioned earlier. The trapezial component implant 130 is also composed of a ceramic material for mating with the ceramic head 128. The head 128 is made removable, since a ceramic material may not be fused onto a cobalt/chrome neck or a titanium neck. The interconnection therefore between the stem component neck and ceramic head 128 is made by providing the stem component implant 120 with a Morse taper neck 126 at its neck-head junction. The Morse taper neck 126 allows the neck of the stem component implant 120 to be secured to the removable ceramic head 128. In this regard, the removable head 128 is provided with a reverse Morse-taper opening indicated generally at 140 as best seen in FIG. 9. The neck 126 and head 128 are joined with a reverse-Morse taper mechanism. It should be understood by those skilled in the art, that because of the hardness of ceramic, one can not press the ceramic head 128 into the trapezial component 130. So the head 128 is built into the trapezial component 130 allowing the neck 126 to be connected to the head 128 by pressing the neck 126 into the reverse Morse-taper opening 140 of the ceramic head 128. Tiny grooves engage between the two parts, the neck 126 and the head 128 so that they cannot be pulled apart without applying an unusual significant amount of force. As a reverse Morse-taper connection is well known to those skilled in the art, it will not be described hereinafter in greater detail.

Figure 10:
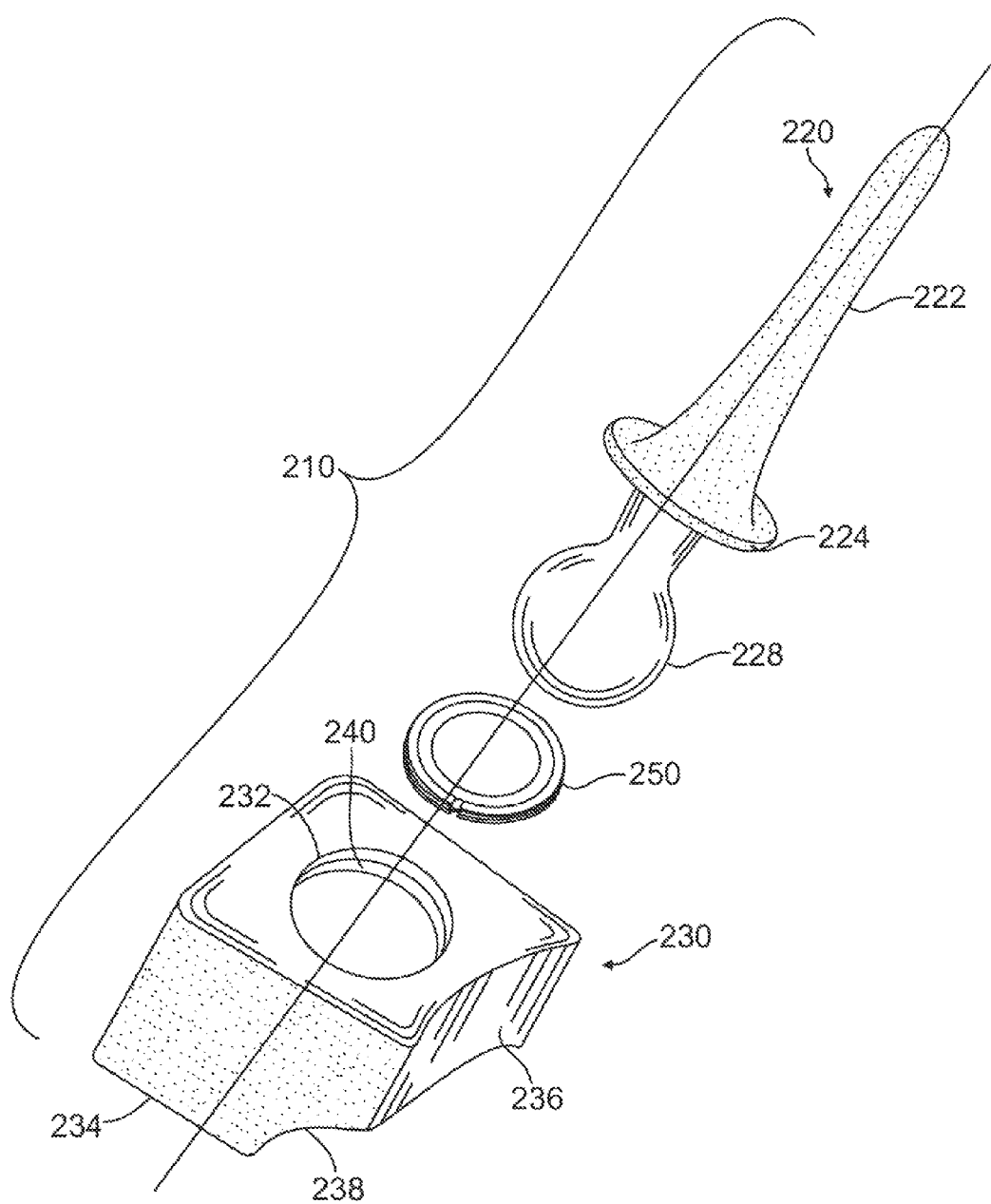
FIG. 10 is a perspective view of yet another customized $1^{st}$ carpometacarpal arthroplasty system constructed according to the present invention.

Referring now to the drawings and more particularly to FIG. 10 there is illustrated a carpometacarpal prosthesis system 210, which is constructed in accordance with the present invention. The prosthesis system 210 is substantially similar to the prosthesis system 10 in that it also generally includes a stem component implant 220 and a trapezial implant 230. The stem component implant 220 is composed of a titanium or cobalt/chrome material while the trapezial component 230 is also composed of either a titanium or cobalt/chrome material or a ceramic material. In this regard the stem component implant 220 has a solid metallic stem 222, metallic collar 224, metallic neck 226 and metallic head 228. In order to allow the metallic head 228 to be locked into the ceramic socket 232 of the ceramic trapezial component 230, the socket 232 is provided with a circular cutout 240 which is dimensioned for receiving therein a locking ring 250. In this regard, as the head 228 is press fit into the socket 232 the locking ring 250 will open a sufficient distance to allow the head 228 to be received within the socket 232 and then the ring 250 will close capturing the head 228 within the socket 232. In this regard, a reverse action would not be possible.

The trapezial component implant 230 is shown with a rough surface, but it should be understood by those skilled in the art, that when the trapezial component 230 is composed of a ceramic material as opposed to a cobalt/chrome material, the trapezial component 230 would not be provided with a rough surface as shown in FIG. 10. As noted earlier, the trapezial component 230 is substantially similar to the trapezial component 30 in that it also includes articulating surfaces, such as a second metacarpal bone articulating surface cut out area 236, a trapezoid bone cutout surface 238 and a scaphoid bone articulating surface area 234, each articulating surface area has a smooth surface with smooth rounded corners to facilitate the articulation actions between the trapezial component 230 and the surrounding bones of the hand such as the second metacarpal bone 501, the trapezoid bone 502 and the scaphoid bone 503.

Figure 11:
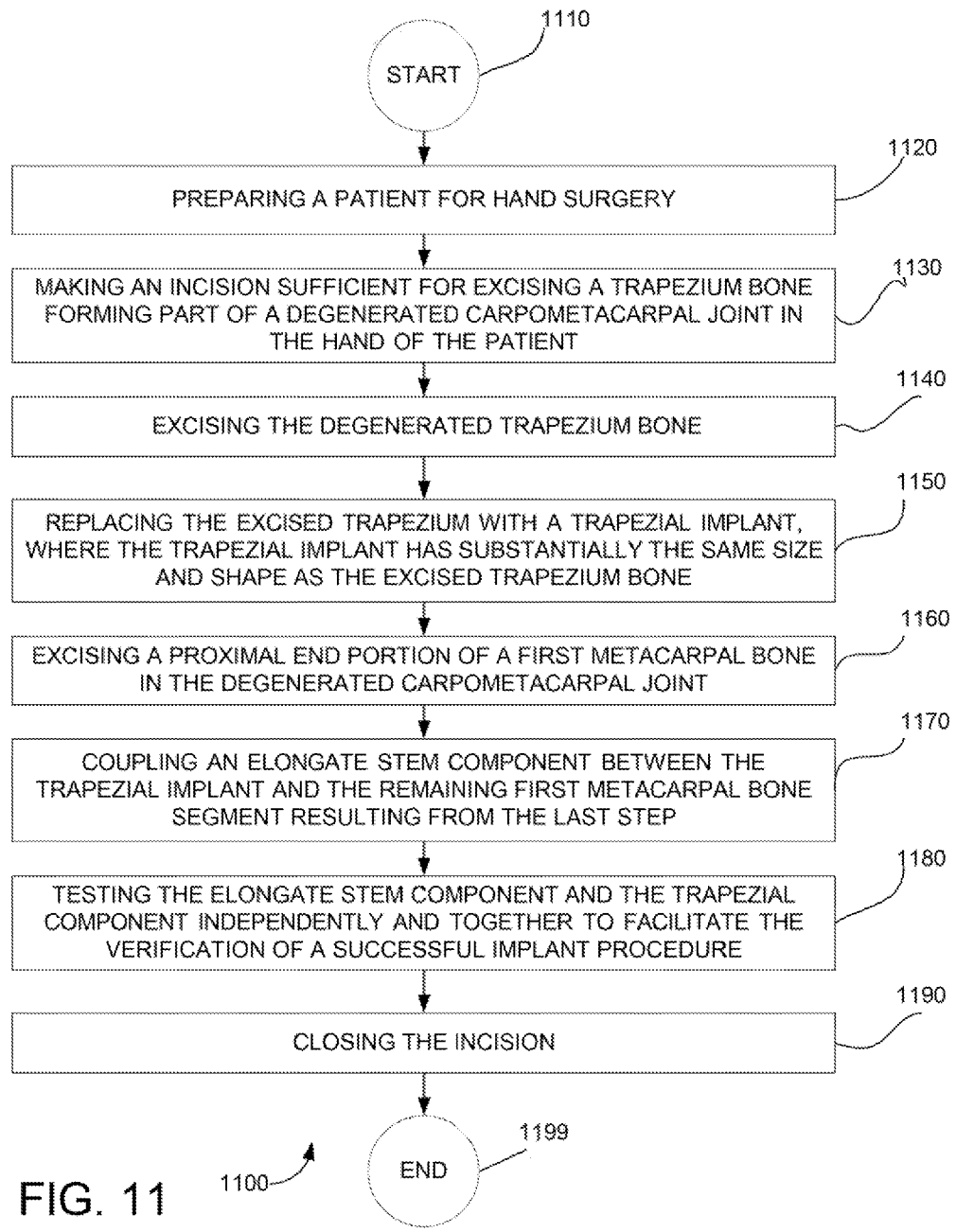
FIG. 11 is flowchart of the implant method for replacing a degenerated carpometacarpal joint of a hand.

Referring now to the drawings and more particularly to FIG. 11 an illustrative method of using 1100 associated with an exemplary embodiment for a first carpometacarpal arthroplasty system 10 will now be described.

The method of using 1100 the system 10 begins at a starting step 1110 when the patient is wheeled into an operating room arena. Once the patient is present in the operating room arena, the procedure dictates that at a preparing step 1120 that the patient is prepared for the implant surgery. Namely, the patient is draped and an anesthesiologist administers the necessary anesthetic agents to render the patient unconscious with a lack of body nerve sensation to facilitate the implant surgical procedure to be described.

When the patient is rendered unconscious, a surgeon at cutting step 1130, makes an incision in the hand of the patient to expose the degenerated carpometacarpal joint in the hand of the patient. Once the incision is made the surgeon works to maintain the ligamentous envelope around the joint by using a small periosteal elevator to remove the tissue off the first metacarpal base and the trapezium bone. Next, at an excising step 1140, the surgeon excises the degenerated trapezium bone. In this regard, the surgeon removes the trapezium bone from the hand of the patient while at the same time making certain not to injury the joint surfaces of the scaphoid bone 503, the trapezoid bone 502, or base of the second metacarpal bone 501 during this step.

When the trapezium bone has been excised, the surgeon trials a trapezial implant at a replacing step 1150 in an effort to facilitate the replacement of the trapezium bone with an trapezial implant 30 that has substantially the same size and shape of the excised trapezium bone. When the surgeon is satisfied that the correct trapezial implant 30 is available, the surgeon at another excising step 1160 excises a proximal end or base portion of the first metacarpal bone 500 to provide the bone with a flat cut-off base surface that exposes the intramedullary canal 500. In this regard, the surgeon may utilize a small oscillating saw to remove about 2-5 mm of bone off the base of the metacarpal. A more preferred amount of bone removed is about 5 mm. While excising the base of the first metacarpal 500, the surgeon will use human retractors to protect the surrounding tissue during this procedure.

After the base of the first metacarpal bone 500 has been excised, the procedure advances to a coupling step 1170 where the surgeon take a trial broach which is substantially smaller then the elongated stem component implant 20 and press fits the trial broach into the intramedullary canal 500A until a proper fit is determined. Then the surgeon using the collar 24 may press fit the stem 22 of the implant into the intramedullary canal 500A for a friction tight fit. In this regard, the stem 22 should not be positioned deeper than about one-half the length of the remaining portion of the first metacarpal bone 500. The stem 22 includes all the necessary surface treatments with a standardized surface roughness proven for excellent bone ingrowth. The collar 24 may stand proud of the flat cut off bone surface of the metacarpal bone 500 so that use of the joint will lead to cyclic loading of the implant bone interface, stimulating bony ingrowth. When the surgeon is satisfied that the implanted stem component 20 will function in a proper manner with the trapezial component implant 30 that has been inserted into the hand of the patient, the surgeon couples the head 28 of the stem component 20 into the receiving socket 32 of the trapezial component 30.

Next at a testing step 1180 the surgeon tests the elongate stem component 20 and the trapezial component 30 to verify that together they provide the thumb of the patient with a maximum arc of 80 degrees in the flexion extension plane. Once the surgeon is satisfied that a successful implant procedure has been accomplished the process advances to a closing step 1190, where the surgeon closes the incision made a step 1130. The procedure is completed at an end step 1199.

In summary then, the method of implanting 1100 a first carpometacarpal system 10 includes the steps of: (a) excising a trapezium forming part of a degenerated carpometacarpal joint; replacing the excised trapezium with a trapezial implant 30, where the trapezial implant 30 has substantially the same size and shape as the excised trapezium; (b) excising a proximal end portion of a first metacarpal forming part of the degenerated carpometacarpal joint; and (c) coupling an elongate stem component 20 between said trapezial implant 30 and a remaining first metacarpal segment 500 resulting from the last mentioned step of excising to facilitate substantially pain free universal moment between the remaining first metacarpal segment and said trapezial implant.

In the above mentioned procedure for helping to diminishing the pain in a degenerated carpometacarpal joint in the hand of the patient the step 1160 of excising a proximal end portion of a first metacarpal 500 includes forming a substantially flat base surface on said remaining first metacarpal segment. Also in this method 1100, the step of coupling 1170 includes: drilling a centrally disposed tapered cavity commencing at the base surface of the remaining first metacarpal 500 and extending inwardly along a longitudinal axis of the remaining first metacarpal 500 a sufficient distance to facilitate receiving in friction-tight fit within the intramedullary canal or cavity 500A at least a portion of the stem 22 of the elongate stem component 20 but not a sufficient distance so that the at least a portion 22 of said elongate stem component 20 extends beyond a midpoint longitudinal plane of the remaining metacarpal segment 500.

From the foregoing, it should be understood by those skilled in the art, that the stem component has either a unitary construction as described herein earlier or a modular-like construction that includes: an elongate tapered body member 122 which is adapted for an intramedullary canal 500A fit within the remaining metacarpal segment 500; a flange like collar 124 integrally connected to a proximal end part of said stem body member 122; a neck-like Morse taper end 126 integrally connected to the collar 124 spaced from said proximal end part of said body member 122; wherein the proximal end of said neck-like Morse taper 126 is adapted to receive thereon a spherical shaped head 128 which is adapted to be coupled to the trapezial component 30.

In the above mentioned procedure for helping to diminishing the pain in a degenerated carpometacarpal joint in the hand of the patient the coupling step 1170 further includes: (a) inserting by press fit said elongate tapered body member 22 into the tapered cavity 500A disposed in the remaining metacarpal segment to help facilitate substantially pain free universal movement between the remaining metacarpal segment 500 and said trapezial component 30; and (b) inserting lockingly by press fit the head 28 of the stem component 20 into a socket 32 disposed in said trapezial implant 30 to further help facilitate substantially pain free universal movement between the remaining metacarpal segment 500 and the trapezial implant 30.

In the above mentioned procedure for helping to diminishing the pain in a degenerated carpometacarpal joint in the hand of the patient the excising steps 1140 of excising a trapezium forming part of the degenerated carpometacarpal joint and the excising step 1160 of excising a proximal end portion of a metacarpal forming part of the degenerated carpometacarpal joint in combination result in the excising of the degenerated carpometacarpal joint.

In the above mentioned procedure for helping to diminishing the pain in a degenerated carpometacarpal joint in the hand of the patient the trapezial implant 30 is composed of a body tolerant material with some surface roughness to facilitate bonding of scar tissue to said trapezial implant.

In the above mentioned procedure 1100 for helping to diminishing the pain in a degenerated carpometacarpal joint in the hand of the patient the head 128 and said neck-like Morse taper 126 are selectively sized relative to the excised portion of said first metacarpal and said excised trapezium to facilitate restoring a normal length thumb with relation to a thumb being partially excised for the prosthesis system 110.

In the above mentioned procedure 1100 for helping to diminishing the pain in a degenerated carpometacarpal joint in the hand of the patient the coupling step 1170 of inserting by press fit the elongate tapered body member 22 into the tapered cavity 500A disposed in the remaining metacarpal segment 500 includes: (a) positioning the flanged collar 24 proud of the substantially flat base surface on the remaining first metacarpal segment 500 so that cyclic loading of a resulting implant bone interface between the remaining first metacarpal segment 500 and the collar 24 will stimulate bony ingrowth therebetween.

In the above mentioned procedure 1100 for helping to diminishing the pain in a degenerated carpometacarpal joint in the hand of the patient the elongate tapered body member 22 or 122 or 222 is a grit-blasted tapered body member.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. For example, rather than having as disclosed a neck-head junction with a replaceable head it is contemplated that a unitary ceramic neck-head configuration could be provided using a reverse Morse taper head-neck to collar interconnection allowing the unitary ceramic neck and head to be attached to a metallic collar have a short metallic neck extending therefrom to enable the reverse Morse taper connection. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the following claims.

Therefore, provided herein are a new and improved carpometacarpal prosthesis system and a novel method of using the system 10, which effectively restores in a much more efficient and less time consuming manner substantially normal thumb function following the effects of injury to or disease in the carpometacarpal joint of the thumb.

I claim:

1. A prosthesis for use in a carpometacarpal prosthesis system, comprising:
a non-resorbable trapezial implant for replacing a removed trapezium, wherein the trapezial implant is selected from a group of body tolerant materials consisting of; polyethylene, titanium, a cobalt/chrome alloy or a ceramic, said trapezial implant configured to help replicate a natural first metacarpal motion in three planes of motion when coupled to a partially excised first metacarpal bone in a hand of the removed trapezium; and
a first metacarpal implant for coupling said trapezial implant to said partially excised first metacarpal bone and enabling said trapezial implant and said partially excised first metacarpal bone to cooperate with one another to carry out natural thumb motions of adduction, abduction and opposition;
wherein the first metacarpal implant has a unitary construction including a tapered distal end portion for implanting into the partially excised first metacarpal bone, a flanged collar for abutment against a proximal end of the partially excised first metacarpal bone, an elongated neck having a length selected to restore the partially excised first metacarpal bone to an original length before the first metacarpal bone was partially excised and a spherical head configured to couple the first metacarpal implant to the trapezial implant to replicate natural thumb motion between the first metacarpal implant and the trapezial implant;
wherein the distal end portion, the flanged collar, the elongated neck and the spherical head are aligned along one common, central longitudinal axis.

2. The prosthesis, according to claim 1, wherein said distal end portion is composed of a material with a surface texture that facilitates bone ingrowth; and
wherein said surface texture is porous.

3. A carpometacarpal prosthesis system, comprising:
a non-resorbable trapezial implant with a plurality of surfaces including a scaphoid bone interaction surface, a trapezoid bone interaction surface; and a second metacarpal bone interaction surface, wherein the trapezial implant is selected from a group of body tolerant materials consisting of; polyethylene, titanium, a cobalt/chrome alloy or a ceramic;
wherein each of the plurality of surfaces is configured to enable said trapezial implant to replicate a natural free articulating motion when implanted to replace an excised trapezium bone; and
a first metacarpal implant having a proximal end for lockingly engaging onto said trapezial implant, said first metacarpal implant having a length dimension configured to replicate, in cooperation with said trapezial implant, natural adduction, abduction, and opposition motions, when implanted to replace an excised portion of a first metacarpal bone,
wherein the first metacarpal implant has a unitary construction including a tapered distal end portion for implanting into the excised portion of the first metacarpal bone, a flanged collar for abutment against a proximal end of the excised portion of the first metacarpal bone, an elongated neck having a length configured to correspond to that portion of bone excised from the proximal end of the first metacarpal bone to restore the first metacarpal bone to an original length before the proximal end of the first metacarpal bone was excised and a spherical head configured to couple the first metacarpal implant to the trapezial implant to provide natural thumb motion between the first metacarpal implant and the trapezial implant;
wherein the distal end portion, the flanged collar, the elongated neck and the spherical head are aligned along one common, central longitudinal axis.

4. The carpometacarpal prosthesis system according to claim 3, wherein said trapezial implant is configured to a same size and shape of said excised trapezium bone in order to facilitate replacement of the excised trapezium bone with said trapezial implant and configured to help replicate natural first metacarpal motion in three planes of motion when the trapezial implant is coupled to the first metacarpal implant;
wherein said first metacarpal implant is configured to couple said trapezial implant to said excised portion of the first metacarpal bone and further configured to help said trapezial implant and said excised portion of the first metacarpal bone to cooperate with one another to permit the adduction, abduction and opposition motions;
wherein said distal end portion is composed of a material with a surface texture that facilitates bone ingrowth; and
wherein said surface texture is porous.

5. The carpometacarpal prosthesis system, according to claim 4, wherein said distal end portion is composed of a body tolerant material selected from a group of body tolerant materials consisting of; cobalt/chrome, titanium, tantalum or a nickel alloy.

6. The carpometacarpal prosthesis system, according to claim 3, wherein said scaphoid bone interaction surface, said trapezoid bone interaction surface; and said second metacarpal bone interaction surface are smooth articular surfaces configured to help replicate the natural free articulating motion of an excised trapezium bone when the excised trapezium bone is replaced with said trapezial implant.

7. A carpometacarpal prosthesis system, comprising:
a first metacarpal implant for replacing a partially excised first metacarpal bone and for restoring the partially excised first metacarpal bone to substantially its original length enabling the first metacarpal implant in combination with the partially excised first metacarpal bone to carry out natural thumb motions of adduction, abduction and opposition,
wherein the first metacarpal implant has a unitary construction including a tapered distal end portion for implanting into the partially excised first metacarpal bone, a flanged collar for abutment against a proximal end of the partially excised first metacarpal bone, an elongated neck having a length selected to restore the first metacarpal bone to an original length before the proximal end portion of the first metacarpal bone was partially excised and a spherical head configured to couple the first metacarpal implant to the trapezial implant to replicate natural thumb motion between the first metacarpal implant and the trapezial implant, wherein the distal end portion, the flanged collar, the elongated neck and the spherical head are aligned along one common, central longitudinal axis; and a freely articulating trapezial implant for replacing an excised trapezium and for coupling to the first metacarpal implant to permit the freely articulating trapezial implant, in response to motions of adduction, abduction and opposition, to articulate freely in natural articulating motions relative to a plurality of articular bone surfaces including a scaphoid bone articular surface, a trapezoid bone articular surface, and a second metacarpal bone articular surface, wherein the trapezial implant is selected from a group of body tolerant materials consisting of; polyethylene, titanium, a cobalt/chrome alloy or a ceramic.

8. The carpometacarpal prosthesis system, according to claim 7, wherein said flanged collar is disposed adjacent to said partially excised first metacarpal bone so that cyclic loading of an implant bone interface between said partially excised first metacarpal bone and said flanged collar will stimulate bony ingrowth there between.

9. The carpometacarpal prosthesis system, according to claim 7, wherein said flanged collar has a sufficient diameter to facilitate press fitting of said distal end portion into an elongated, centrally disposed, tapered cavity formed in the first metacarpal bone.

10. The carpometacarpal prosthesis system, according to claim 7, wherein said trapezial implant cooperates with a proximal surface area of a trapezoid bone to form a concave surface for articulation with a convex distal articular surface area of a scaphoid bone to facilitate pain free movement between said trapezial implant and the scaphoid bone and the trapezoid bone.

11. The carpometacarpal system, according to claim 7, wherein said trapezial implant is composed of a body tolerant material with some surface roughness to facilitate bonding of scar tissue to said trapezial implant; and wherein a base portion of said trapezial implant is configured to stimulate a natural anatomy to articulate within a convex distolateral surface area of a scaphoid bone to facilitate pain free movement between said trapezial implant and the scaphoid bone.

* * * * *